United States Patent
Rauch et al.

(10) Patent No.: US 10,470,731 B2
(45) Date of Patent: Nov. 12, 2019

(54) BOLUS IMAGING

(71) Applicant: Siemens Healthcare GmbH, Erlangen (DE)

(72) Inventors: John Christopher Rauch, Mesa, AZ (US); Martin Trini, Schaumburg, IL (US)

(73) Assignee: Siemens Healthcare GmbH, Erlangen (DE)

( * ) Notice: Subject to any disclaimer, the term of this patent is extended or adjusted under 35 U.S.C. 154(b) by 80 days.

(21) Appl. No.: 15/825,002

(22) Filed: Nov. 28, 2017

(65) Prior Publication Data
US 2018/0168529 A1 Jun. 21, 2018

(30) Foreign Application Priority Data
Dec. 20, 2016 (EP) .................................... 16205405

(51) Int. Cl.
*G06K 9/00* (2006.01)
*A61B 6/00* (2006.01)
(Continued)

(52) U.S. Cl.
CPC .............. *A61B 6/481* (2013.01); *A61B 6/032* (2013.01); *A61B 6/463* (2013.01); *A61B 6/486* (2013.01); *A61B 6/503* (2013.01); *A61B 6/504* (2013.01); *A61B 6/5235* (2013.01); *A61B 6/541* (2013.01); *A61K 49/0433* (2013.01); *H05G 1/60* (2013.01); *H05G 1/64* (2013.01); *A61B 6/4441* (2013.01)

(58) Field of Classification Search
CPC .............................. A61B 6/463; A61B 6/4441
See application file for complete search history.

(56) References Cited

U.S. PATENT DOCUMENTS 5,851,184 A 12/1998 Goethel
6,639,211 B1 * 10/2003 Anand ................. G01R 33/561
250/282
(Continued)

FOREIGN PATENT DOCUMENTS

DE        41 33 018         4/1993
WO      20030101300      12/2003

OTHER PUBLICATIONS

Ernst, Klotz et al., "Perfusion measurements of the brain: using dynamic CT for the quantitative assessment of cerebral ischemia in acute stroke", European Journal of Radiology, Elsevier Science, NL, vol. 30, No. 3, 1 Jun. 1999, pp. 170-184.
(Continued)

*Primary Examiner* — Oneal R Mistry

(57) ABSTRACT

A system and method includes detection of a trigger event, automatic injection, in response to detecting the trigger event, of a bolus of contrast medium into a patient volume after expiration of a predetermined injection delay period, automatic acquisition, in response to detecting the trigger event, of a plurality of images after expiration of a predetermined imaging delay period, where two or more of the plurality of images comprise an image of the bolus at respective different locations within vasculature of the patient volume, generation of a composite image based on the plurality of images, the composite image including a representation of the vasculature of the patient volume, and display of the composite image.

19 Claims, 9 Drawing Sheets

(51) Int. Cl.
    *A61K 49/04*      (2006.01)
    *H05G 1/64*      (2006.01)
    *H05G 1/60*      (2006.01)
    *A61B 6/03*      (2006.01)

(56) References Cited

U.S. PATENT DOCUMENTS

| | | | |
|---|---|---|---|
| 2008/0130824 A1 | 6/2008 | Fujisawa | |
| 2009/0010516 A1* | 1/2009 | Boese | A61B 90/36 382/131 |
| 2015/0157231 A1* | 6/2015 | Gillberg | A61B 5/0408 600/523 |
| 2015/0201894 A1* | 7/2015 | Baumgart | A61B 6/481 378/62 |

OTHER PUBLICATIONS

Cimen, Serkan, et al., "Reconstruction of coronary arteries from X-ray angiography: a review", Medical Image Analysis, Oxford University Press, Oxford GB, vol. 32, 11 Mar. 2016, pp. 46-68.
EP Search Report dated Oct. 6, 2017 from counterpart application No. 16205405.0, 14 pages.

* cited by examiner

BOLUS IMAGING

BACKGROUND

According to conventional angiographic x-ray imaging, contrast media are used to enhance the contrast of blood-carrying structures within patient anatomy. For example, a contrast medium is introduced into a patient volume (e.g., via intravenous injection) and an x-ray image of the volume is acquired while the medium resides within blood-carrying structures of the volume. In the x-ray image, structures which contain the medium (e.g., veins, arteries, capillaries) appear darker than they would otherwise appear.

Systems are desired for generating images of patient vasculature using reduced amounts of contrast media.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Some embodiments facilitate the generation of images of patient vasculature. According to some embodiments, a small bolus of contrast medium is injected intravenously and images are acquired in synchronization with the injection. The images are then combined to create a composite image which portrays the vasculature through which the small bolus traveled during acquisition of the images. The images may be acquired over several cardiac cycles, in which case the synchronization may take into account the length and/or phases of the cardiac cycle.

Figure 1:
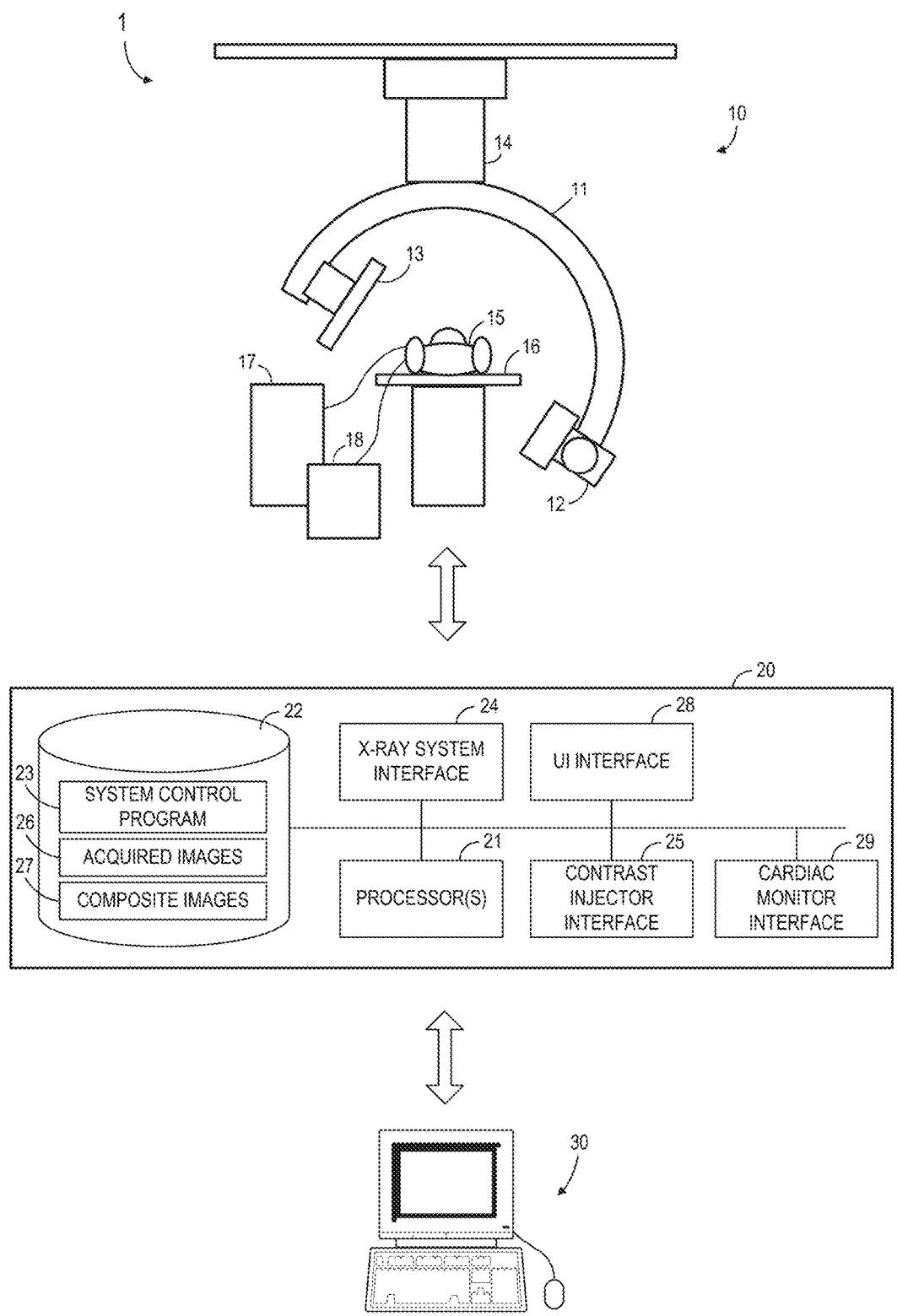
FIG. 1 illustrates a system according to some embodiments.

FIG. 1 illustrates system 1 according to some embodiments. System 1 includes x-ray imaging system 10, control and processing system 20, and operator terminal 30. Generally, and according to some embodiments, x-ray imaging system 10 introduces contrast medium into a patient volume and acquires x-ray images of the patient volume. Control and processing system 20 controls x-ray imaging system 10 and receives the acquired images therefrom. Control and processing system 20 processes the images as described below and provides the processed images to terminal 30 for display thereby. Such processing may be based on user input received by terminal 30 and provided to control and processing system 20 by terminal 30.

X-ray imaging system 10 comprises C-arm 11 on which radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween. Embodiments are not limited to C-arm-based imaging systems.

Radiation source 12 may comprise any suitable radiation source, including but not limited to a Gigalix™ x-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 13 may therefore represent a two-dimensional projection image of these tissues.

Contrast injector 17 may comprise any known device or devices suitable to controllably introduce contrast medium into a patient volume. Such control includes control over the timing, the rate, and the quantity of introduced contrast medium. As described above, structures which contain contrast medium appear darker in x-ray images than they would otherwise appear. Conversely, if a "negative" contrast agent (e.g., $CO_2$) is used, structures which contain contrast medium appear lighter in x-ray images than they would otherwise appear. Contrast injector 17 may include a reservoir for each of one or more contrast media, and a patient interface such as medical-grade tubing terminating in a hollow needle.

Cardiac monitor 18 may comprise any known system to detect cardiac signals of patient 15. Cardiac monitor 18 may be coupled to patient 15 via one or more electrodes. Cardiac monitor 18 may comprise an electrocardiograph according to some embodiments.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to move C-arm 14, to cause radiation source 12 to emit radiation, to control detector 13 to acquire an image, to cause injector 17 to introduce contrast medium into a volume of patient 15, and to perform any other function. In this regard, system 20 includes x-ray system interface 24, contrast injector interface 25, and cardiac monitor interface 29 for communication with system 10.

Images acquired from system 10 are stored in data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, contrast medium bolus injection profile, x-ray tube voltage, image resolution and radiation dosage.

Processor(s) 21 may execute system control program 23 to process acquired images 26, resulting in processed images 27. Processed images 27 may be provided to terminal 30 via UI interface 28 of system 20. UI interface 28 may also receive input from terminal 30, which is used to control processing of acquired images 26 as described below.

Terminal 30 may simply comprise a display device and an input device coupled to system 20. Terminal 30 displays acquired images 26 and/or processed images 27 received from system 20 and may receive user input for controlling display of the images, operation of imaging system 10, and/or the processing of acquired images 26. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2:
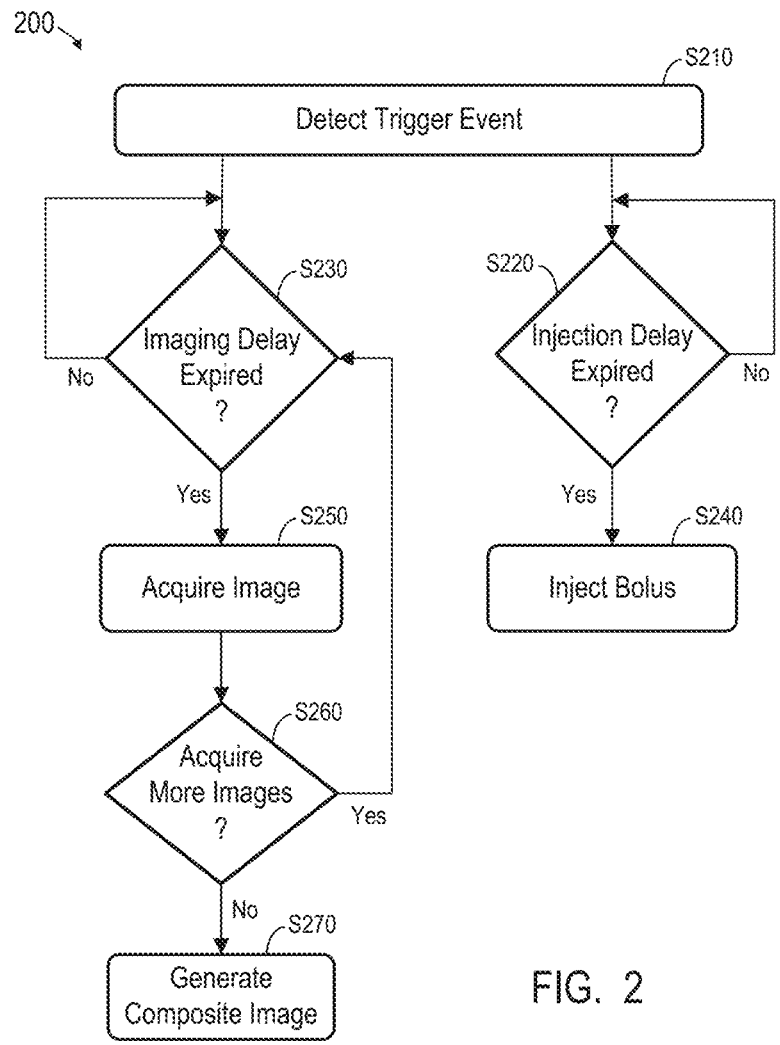
FIG. 2 is a flow diagram of a process according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of system 1, but embodiments are not limited thereto.

It will be assumed that, prior to S210, the patient is positioned for imaging according to known techniques. For example, and with reference to the elements of system 1, patient 15 is positioned on table 16 to place a particular volume of patient 15 between radiation source 12 and radiation detector 13. Table 16 may be adjusted to assist in positioning the patient volume as desired. As is known in the art, such positioning may be based on a location of a volume of interest, on positioning markers located on patient 15, on a previously-acquired planning image, and/or on a portal image acquired after an initial positioning of patient 15 on table 16.

Initially, at S210, a trigger event is detected. Detection of the trigger event may comprise reception of an instruction from an operator of terminal 30 to commence imaging a patient, or detection of a physical state of the patient, such as but not limited to maximum exhalation (i.e., a state associated with reduced respiration-induced vessel motion).

At S220, it is determined whether an injection delay period has expired. The injection delay period is a time period which is to pass after a trigger event before commencing injection of a bolus of contrast medium. The injection delay period may be zero, or may be set to an amount, based on the nature of the trigger event, which attempts to minimize vessel motion during image acquisition. Flow cycles at S220 until the injection delay period has expired.

Contemporaneously, at S230, it is determined whether an imaging delay period has expired. The imaging delay period is a time period which is to pass after a trigger event before commencing image acquisition. The imaging delay period may be set equal to the injection delay period, less than the injection delay period (e.g., to ensure that an image frame is acquired without contrast medium), or greater than the injection delay period (e.g., to ensure that only image frames with contrast medium are acquired). Flow cycles at S230 until the imaging delay period has expired.

Flow proceeds from S220 to S240 after determining that the injection delay has expired. A bolus of contrast medium is injected into the patient at S240. The duration of the bolus injection is determined based on the desired width of the bolus in the to-be-acquired images. The flow rate of the injection may be selected such that the incoming contrast medium blocks blood flow during the duration of the bolus injection (i.e., the injection flow rate is greater than the flow rate of blood in the vessel(s) being imaged).

The injection duration and injection flow rate determine the quantity of injected contrast medium. Accordingly, the quantity of injected contrast medium may be reduced by reducing either or both of these parameters. However, due to the dependence of the injection flow rate on the blood flow rate according to some embodiments, it may be preferable to reduce the required quantity of contrast medium by selecting an injection duration (i.e., a bolus width) which is as short as needed to result in a suitable composite image, as will be described below.

According to some embodiments of S240, system 20 instructs contrast injector 17 to introduce the bolus of contrast medium into an artery of patient 15. The parameters of the medium introduction (e.g., duration, flow rate, location, volume) may be controlled by system control program 23.

Figure 3:
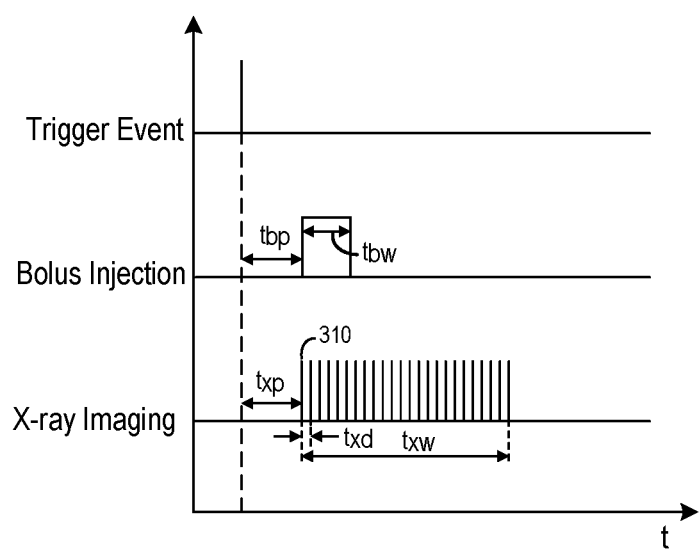
FIG. 3 includes a timing diagram according to some embodiments.

FIG. 3 is a timing diagram illustrating a trigger event, a bolus injection and x-ray imaging according to some embodiments. As shown, the bolus injection is delayed from the trigger event by an injection delay period $t_{bp}$. The acquisition of x-ray images is delayed from the trigger event by an imaging delay period $t_{xp}$. As described above, these periods need not be of equal duration according to some embodiments. The duration of bolus injection is shown as period $t_{bw}$. As also described above, period $t_{bw}$ may be selected to provide a suitable bolus width within the acquired images according to some embodiments.

In this regard, and returning to process 200, an x-ray image is acquired at S250 after the imaging delay is determined to have expired at S230. Acquisition of the image is represented by line 310 of FIG. 3. According to some embodiments of S250, C-arm 11 is positioned so that radiation source 12 and radiation detector 13 are disposed at a predetermined projection angle with respect to the patient volume. Radiation source 12 is instructed to emit x-ray radiation toward radiation detector 13 based on parameters (e.g., x-ray tube voltage, dosage) controlled by system control program 23 as is known in the art. Radiation detector 13 receives the emitted radiation and produces a set of data (i.e., a projection image) at S250. The projection image may be received by system 20 and stored among acquired images 26.

At S260, it is determined whether additional images are to be acquired. This determination may be based on a predetermined plan which specifies a number of images and their respective timings, and/or a predetermined imaging time period during which images are to be acquired at regular intervals. If additional images are to be acquired, flow returns to S230 to wait for an imaging interval associated with a next image to be acquired.

The timing diagram of FIG. 3 illustrates imaging interval $t_{xd}$ according to some embodiments. Flow pauses at S230 for interval $t_{xd}$ prior to acquiring a next image at S250. The duration of imaging period $t_x$ may be set to substantially equal a time required for the bolus to pass through the region of interest. As shown in the timing diagram, flow returns from S260 to S230 and S250 twenty-one additional times to acquire twenty-one additional images at the illustrated timings. Flow advances to S270 after a last image is acquired.

A composite image is generated from two or more of the acquired images at S270. According to some embodiments, all of the acquired images are used in the generation of the composite image. The composite image may, in some embodiments, provide an indication of the vasculature through which the bolus traveled during acquisition of the images. The composite image may be stored among composite images 27 of storage device 22.

According to some embodiments, the acquired images are registered with one another during generation of the composite image at S270. Registration is intended to remove motion artifacts between the images of a pair, by correcting for any relative motion of the patient between acquisitions of the images of the pair. Any motion correction technique may be employed at S270. Moreover, visual characteristics of the images may be matched at S270. Such matching may include modifying one or more images to match a brightness, contrast, signal strength and/or other visual characteristic of another image. S270 may comprise histogram matching in some embodiments.

Figure 4:
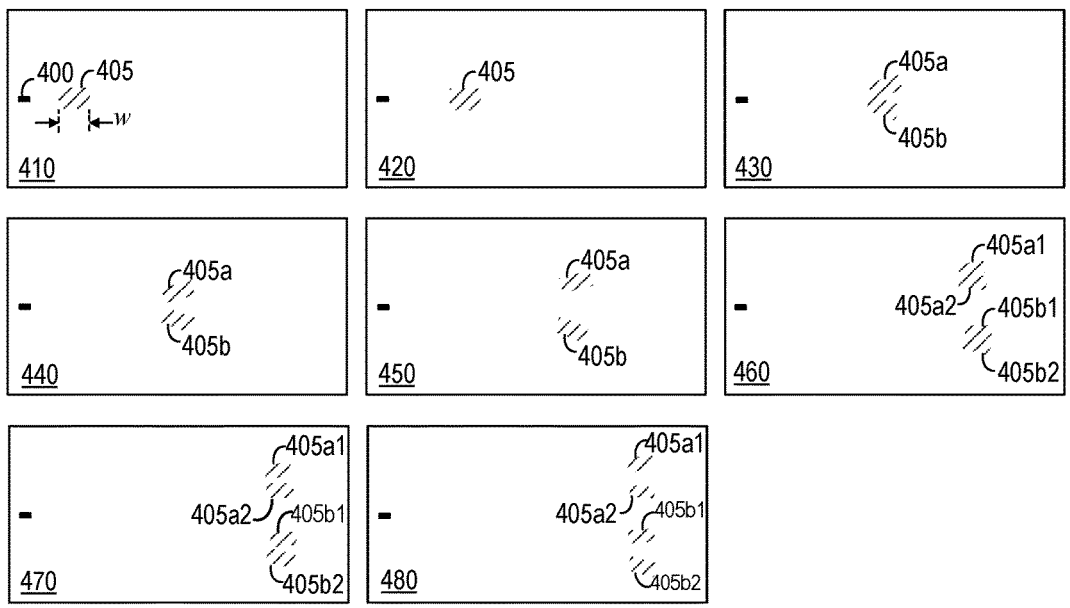
FIG. 4 illustrates x-ray images acquired according to some embodiments.

FIG. 4 illustrated images 410 through 480 which are acquired at S250 according to an example of some embodiments. Image 410 may comprise a first image acquired at S250 after detection of a trigger event and expiration of the imaging delay period. Image 410 depicts injection needle 400 and bolus 405. As described above, a duration period $t_{bw}$ of the bolus injection may have been determined so as to create bolus 405 of width w.

Image 420 is assumed to have been acquired after an imaging delay period $t_{xd}$. Accordingly, bolus 405 has advanced through the imaged patient volume, presumably along a path of an artery in which bolus 405 resides. It should be noted that the width, height and/or shape of bolus 405 may differ among the acquired images due to dispersal of the contrast medium, or due to change in the shape of the vasculature cross-section in the plane of the image. Such a change in shape may comprise an actual widening or narrowing of the vasculature or "foreshortening" caused by variations in the skew of the vasculature with respect to the plane of the image.

Image 430 illustrates the break-up of bolus 405 into portions 405a and 405b due to branching of the vasculature. Images 440, 450 and 460, acquired successively over time, depict further movement of bolus portions 405a and 405b. Lastly, images 460, 470 and 480 depict further break-up of portions 405a and 405b into portions 405a1, 405a2, 405b1 and 405b2 and movement thereof according to some embodiments.

Figure 5:
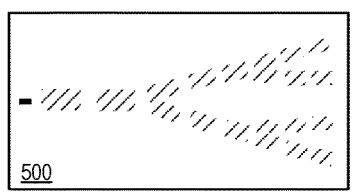
FIG. 5 illustrates a composite x-ray image according to some embodiments.
Figure 6:
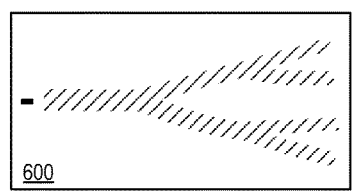
FIG. 6 illustrates a composite x-ray image according to some embodiments.

FIG. 5 illustrates composite image 500 according to some embodiments. Composite image 500 is generated at S270 by combining images 410 through 480. Composite image 500 provides a representation of the vasculature through which bolus 405 passed during the imaging process. As shown, the distance traveled by bolus 405 between the acquisition of images (i.e., during interval $t_{xd}$) is greater than the width w of bolus 405. Accordingly, composite image 500 includes gaps.

In contrast, composite image 600 was generated based on images for which the imaging interval $t_{xd}$ was less than a time required for bolus 405 to travel a distance w. As a result, each image of bolus 405 from one of the acquired images overlaps an image of bolus 405 from a successively-acquired image. Composite image 600 therefore includes no gaps.

Any algorithm for creating an image based on two or more images may be employed at S270. For example, according to some embodiments, a value of each pixel of composite image 500 or composite image 600 is equal to the maximum value of corresponding pixels of each acquired image (i.e., $C_{xy}$=Max $[A1_{x,y}, A2_{x,y}, \ldots, An_{x,y}]$). In some embodiments, the value of each pixel is a weighted sum of corresponding pixels such as $C_{xy}=wkA_{x,y}+(1-w)V_{x,y}$.

Accordingly, some embodiments efficiently provide a representation of patient vasculature while reducing patient exposure to contrast medium with respect to conventional systems.

According to some embodiments, a two-dimensional mask image is acquired at the imaging projection angle prior to the detection of the trigger event at S210. Since the mask image is acquired without the presence of the contrast medium, the mask image depicts background anatomic detail of the patient volume. The mask image may be registered with and subtracted from each of the acquired images prior to combination thereof at S270. The resulting composite image portrays only the vessel components of the patient volume which include contrast medium. Any other processing may be applied to the acquired images prior to generation of the composite image based thereon.

Similarly, any processing that is or becomes known may be applied to the composite image such as, but not limited to, edge enhancement, brightness adjustment, field of view collimation, and conformance of the image to the display properties of the display device of terminal 30. Processing at S270 may include one or more of denoising filters, median filters and low-pass filters.

Figure 7:
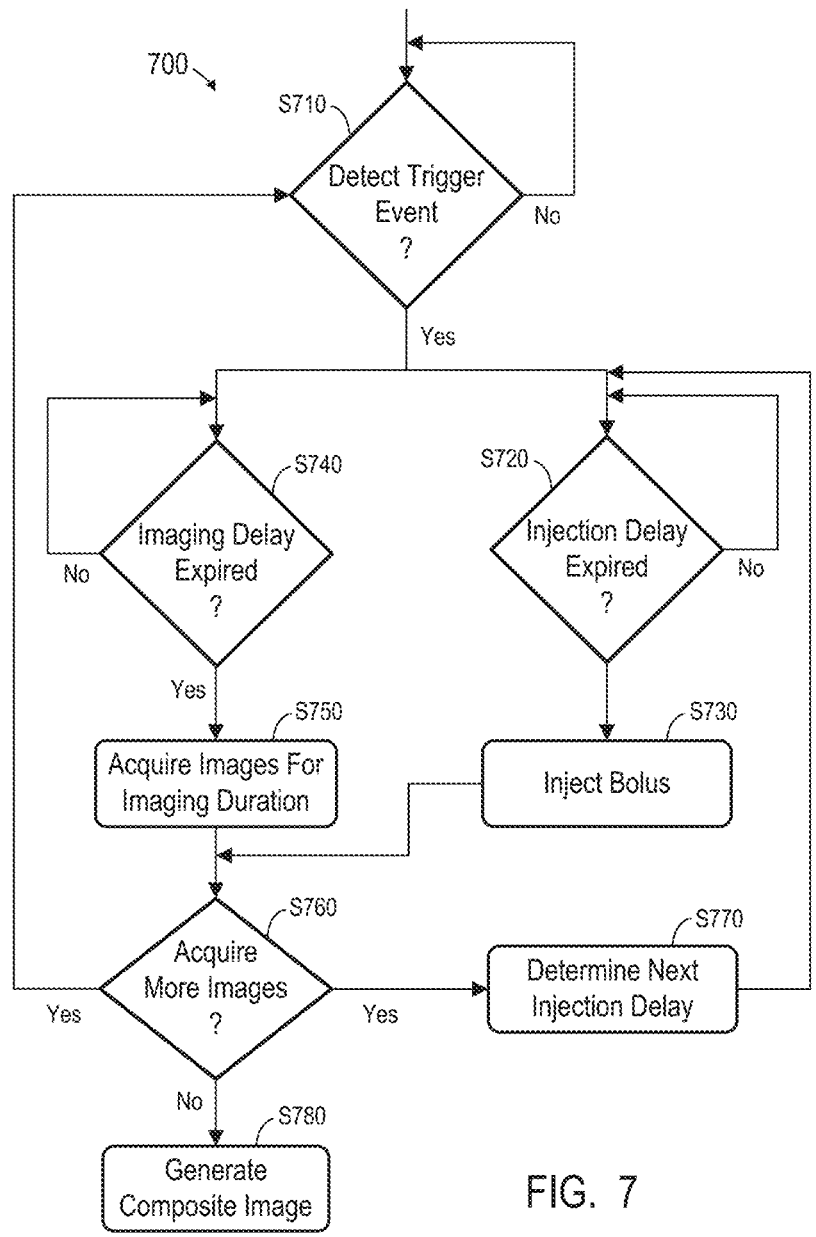
FIG. 7 is a flow diagram of a process according to some embodiments.

Process 700 of FIG. 7 provides vascular imaging according to some embodiments. Process 700 may facilitate imaging of the heart muscle at rest. According to some embodiments, a small bolus of contrast medium is injected and images are acquired as the bolus moves through patient vasculature. Moreover, the images are acquired during rest periods of the cardiac cycle.

A patient is positioned for imaging prior to S710 according to known techniques. Flow pauses at S710 until a trigger event is detected. According to some embodiments, detection of the trigger event may comprise detection of an R-wave peak in an electrocardiogram signal received from cardiac monitor 18.

At S720, it is determined whether an injection delay period has expired. As described with respect to S220 of process 200, flow cycles at S720 until the injection delay period has expired. A bolus of contrast medium is injected into the patient at S730 after expiration of the injection delay period, based on a duration and flow rate determined as described above.

Figure 8:
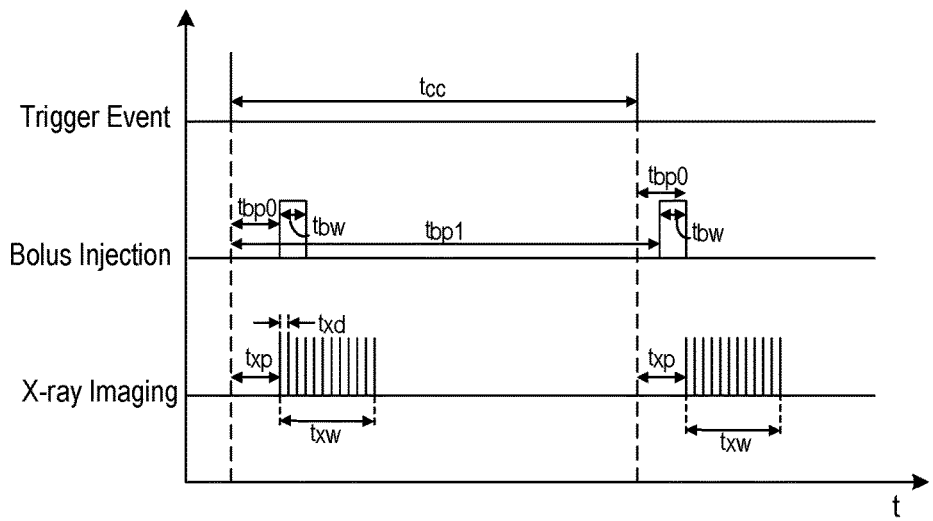
FIG. 8 includes a timing diagram according to some embodiments.

FIG. 8 is a timing diagram illustrating a trigger event and an injection delay period according to some embodiments of process 700. The bolus injection at S730 is delayed from the trigger event by an injection delay period $t_{bp0}$. Process 700 may employ several injection delay periods, which will be generally labelled as $t_{bpN}$. The duration of bolus injection is shown as period $t_{bw}$. As described above, period $t_{bw}$ may be selected to provide a suitable bolus width within the acquired images according to some embodiments.

Also in response to detection of the trigger event, it is determined at S740 whether an imaging delay period has expired. X-ray images are acquired at S750 after expiration of the imaging delay period. As shown in FIG. 8, the acquisition of x-ray images at S750 occurs over imaging period $t_{xw}$ at imaging interval $t_{xd}$ and is delayed from the trigger event by an imaging delay period $t_{xp}$. As described above, $t_{xp}$ and $t_{bpN}$ need not be of equal duration according to some embodiments.

Figure 9:
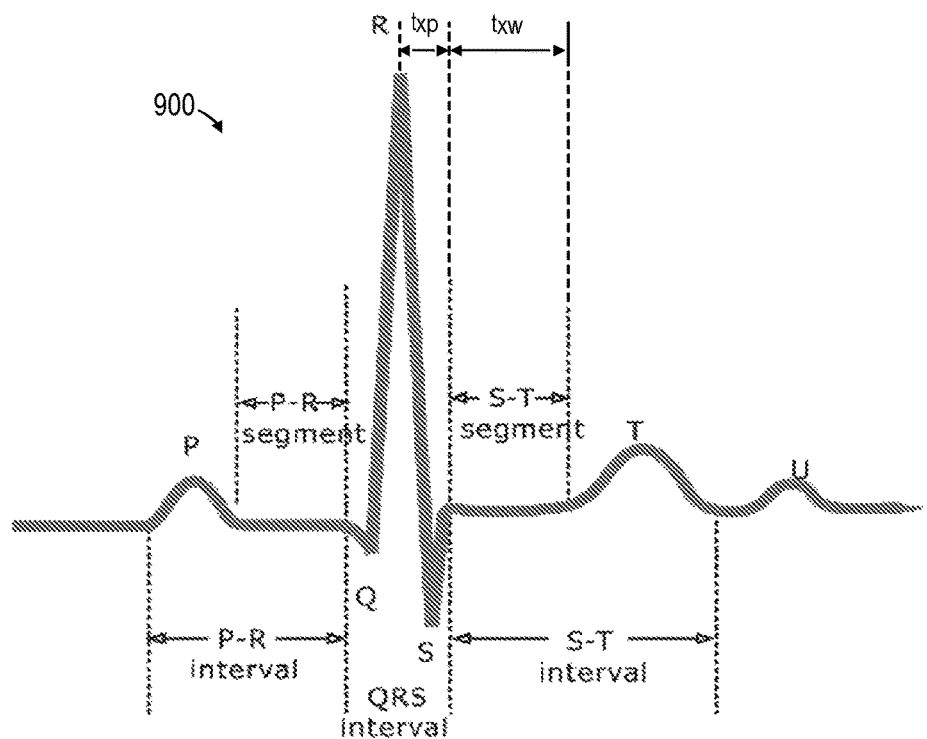
FIG. 9 illustrates a cardiac cycle.

Some embodiments of process 700 attempt to acquire images during a rest period of the cardiac cycle. In this regard, as illustrated with respect to cardiac cycle 900 of FIG. 9, $t_{xp}$ may be set based on the delay between the R-wave peak and the start of the S-T segment. Moreover, the imaging period $t_{xw}$ may be set based on the duration of the S-T segment.

A single imaging period $t_{xw}$ might not provide sufficient time for the bolus to travel through the entire structure of interest. Accordingly, it may be determined to acquire more images at S760 to ensure that the entire structure is imaged. If so, flow returns to S710 to detect a next trigger event (e.g., the R-wave peak) and to acquire a second set of images based on the imaging delay period $t_{xp}$ and the imaging period $t_{xw}$ as described above. FIG. 8 illustrates such an acquisition of second images based on the next trigger event according to some embodiments.

As shown in FIG. 8, a second bolus is injected to be imaged within the second set of images. However, if the injection of the second bolus is delayed $U_{bp0}$ from the next trigger event, the second bolus would travel through a same section of vasculature during acquisition of the second set of images as was traveled by the first bolus during acquisition of the first set of images. Accordingly, a next bolus injection delay is determined at S770 in order to ensure that the second bolus travels through at least a different section of the vasculature during acquisition of the second set of images.

The next injection delay may be determined as to shift the injection to occur before the next R-wave. In some embodiments, the next injection delay is determined as: $t_{bpN} = t_{cc} t_{bp0} - (N*t_{bw})$, where $t_{cc}$ is the period of the cardiac cycle and N is the number of the cardiac cycle being imaged (the second cardiac cycle being number 1). With reference to FIG. 8, $t_{bp1}$ is illustrated as equal to $t_{cc} + t_{bp0} - t_{bw}$. $t_{bp1}$ is shown as measured from the first trigger event. Accordingly, flow returns from S770 to S720 rather than to S710 to determine whether the injection delay time $t_{bp1}$ has expired since the first detected trigger event.

Flow advances to S780 after a last set of images is acquired. A composite image is generated at S780 from two or more (e.g., all) of the acquired images. The composite image may be generated in any suitable manner including but not limited to those described above with respect to S270. The composite image, in some embodiments, may provide an indication of the vasculature through which the bolus traveled during acquisition of the images. The composite image may be stored among composite images 27 of storage device 22.

Figure 10:
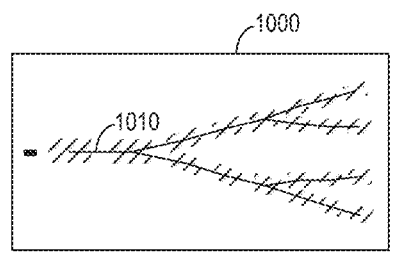
FIG. 10 illustrates a composite x-ray image according to some embodiments.
Figure 11:
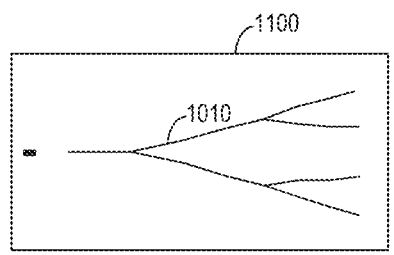
FIG. 11 illustrates a composite x-ray image according to some embodiments.

A composite image generated according to some embodiments may include visualizations which were not present in the acquired images, but which may be derived therefrom. For example, image 1000 of FIG. 10 includes image 500 of FIG. 5 and vascular skeleton 1010 superimposed thereon. Skeleton 1010 may be determined by determining the centroid of each representation of the bolus within image 500 and connecting these centroids with lines or curves (e.g., splines). FIG. 11 illustrates composite image 1100 including skeleton 1010 computed based on the bolus representations of image 500 but not including the bolus representations.

Figure 12:
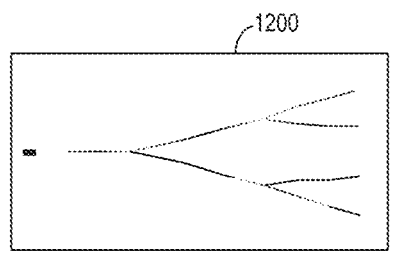
FIG. 12 illustrates a composite x-ray image according to some embodiments.

In another embodiment, time values may be represented on the vessel representation (e.g., skeleton). The time values may indicate a time at which the bolus passed a respective position of the vessel representation. FIG. 12 illustrates composite image 1200, in which color and/or shading of a pixel of skeleton 1210 represents a time at which a bolus (e.g., a centroid of the bolus) passed the portion of the vessel represented by the pixel. Any color and/or shading scheme/scale may be employed according to some embodiments.

Figure 13:
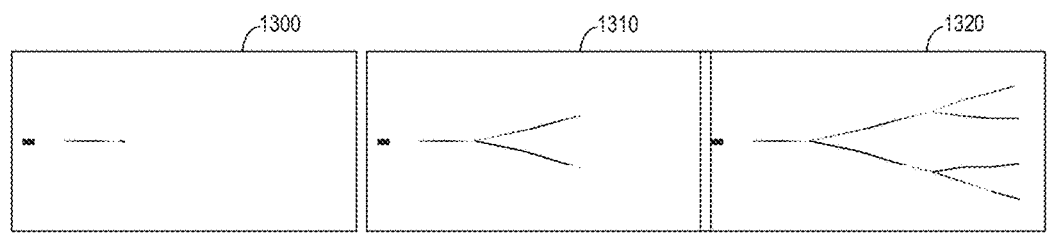
FIG. 13 illustrates looping composite x-ray images according to some embodiments.
Figure 14:
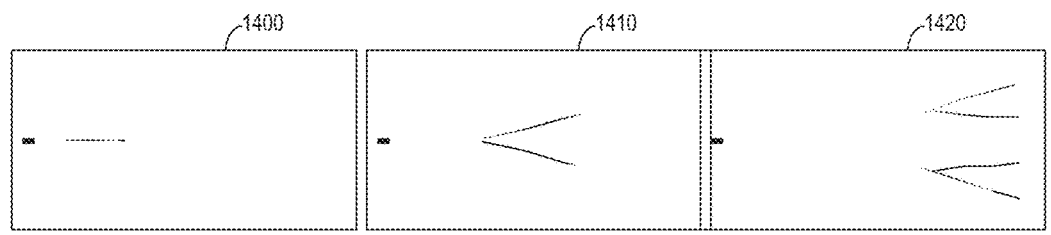
FIG. 14 illustrates looping composite x-ray images according to some embodiments.

FIGS. 13 and 14 each illustrate a series of three looping image frames to illustrate movement of the bolus through the represented vasculature. Images 1300, 1310 and 1320 are cumulative and successively depict an increasing period of time from injection of the bolus. Images 1400, 1410 and 1420 each depict a respective exclusive time period from injection of the bolus. Each image may be color-coded to represent times as described with respect to FIG. 12.

Figure 15:
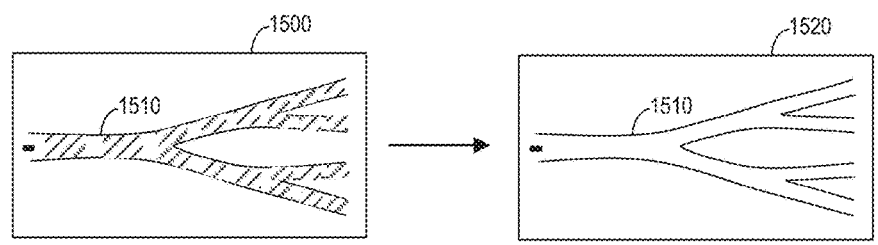
FIG. 15 illustrates generation of a composite x-ray image according to some embodiments.

FIG. 15 illustrates determination of an outer contour of the vasculature through which the bolus has passed. Image 1500 includes the bolus images of image 500 and contour lines 1510 which may be determined therefrom using known image processing techniques. For example, edge detection algorithms may be employed to detect edges of each bolus image which are oriented in the direction of travel of the bolus (i.e., edges which are substantially perpendicular to the direction of travel may be ignored). The detected edges are then connected to create contiguous contours.

Image 1520 illustrates the contours 1510 without the bolus images. A vessel skeleton may be determined based on centerlines of the contours, rather than based on the bolus image centroids as described above. The pixels of the contours may be color-coded to represent a time at which the bolus passed thereby as described with respect to FIGS. 12-14.

The skeleton, contour, and intensity information of the individually-acquired images may be used to automatically generate a plot of vessel diameter at each vessel location. These diameters may be automatically compared with diameter estimates of healthy parent vessels to identify stenotic vessel segments. The contour may also be used as an overlay graphic on a live fluoroscopy image to aid in diagnosis, planning, treatment, and assessment.

Also in view of the determined skeleton and/or the contour of the vessel, the intensity information of the individually-acquired images can be used to determine the amount of foreshortening present at any given point along the vessel tree. For example, if a shrinking of the bolus cross-section and an increase in bolus intensity is noted at a certain vessel location, it can be assumed that the bolus is moving in or out of the plane of the x-ray image at the location. The foreshortening information may be indicated in a composite image (e.g., as a color coding) along with the vessel skeleton and/or vessel contour.

An instantaneous velocity can be estimated for every bolus fragment by evaluating the distance traveled by the bolus between frames and the time between frames. This velocity estimate can be improved by taking into account foreshortening determined based on the change in area of the bolus fragments and the intensity values of the bolus fragments, as described above. Moreover, abnormalities may be flagged at locations at which velocity is reduced but foreshortening is not detected. The velocity information may also be indicated in a composite image (e.g., as a color coding) along with the vessel skeleton and/or vessel contour.

The above-described processes may be extended to three and four dimensions. For example, some imaging systems (e.g., dual-arm systems) are capable of obtaining projection images at two or more different projection angles substantially simultaneously. Using such systems, a set of two (or more) images may be acquired during successive iterations of S250, with each image of a set being associated with a respective projection angles.

Next, at S270, a composite image is created for each projection angle. More specifically, for a particular projection angle, a two-dimensional composite image is created based on the projection images which were acquired at the particular projection angle. Thereafter, using known techniques, a three-dimensional image showing progression of the bolus through the vasculature may be reconstructed based on the two or more composite images.

The following is a description of automatic generation of a three-dimensional skeleton according to some embodiments. First, a two-dimensional skeleton may be determined as described above for each of two two-dimensional composite images associated with different projection angles. Based on the geometry of the imaging system, a position of the first skeleton (associated with a first projection angle) may be matched to one or more positions of the second skeleton (associated with a second projection angle).

A first timestamp is determined of the image frame acquired at the first projection angle in which the bolus first appears at the position of the first skeleton. Second timestamps are also determined of each of the image frames acquired at the second projection angle in which the bolus first appears at the one or more positions of the second skeleton. The second timestamp which most closely matches the first timestamp is identified and its corresponding image frame determines the one of the one or more positions of the second skeleton which most closely matches the first position of the first skeleton. Using these two positions, a corresponding three-dimensional point can be identified. This process may be repeated for other positions of the first skeleton, resulting in an automatically-generated three-dimensional skeleton.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
    a processing unit to:
        detect a trigger event;
        in response to detection of the trigger event, automatically inject a bolus of contrast medium into a patient volume after expiration of a predetermined injection delay period;
        in response to detection of the trigger event, automatically acquire a plurality of images after expiration of a predetermined imaging delay period, two or more of the plurality of images comprising an image of the bolus at respective different locations within vasculature of the patient volume; and
        generate a composite image based on the plurality of images, the composite image including a representation of the vasculature of the patient volume; and
    a display to display the composite image,
    wherein detection of the trigger event comprises detection of a peak of an R-wave in a cardiac signal, wherein the imaging delay period is based on a time between the peak and the start of an S-T interval of the cardiac signal, and wherein the plurality of images are acquired during an S-T segment of the cardiac signal.

2. A system according to claim 1, wherein each of the plurality of images is acquired at a predefined imaging interval, and wherein a distance traveled by the bolus in the vasculature during the predefined imaging interval is greater than a dimension of the bolus in the direction of travel.

3. A system according to claim 1, wherein generation of the composite image comprises:
    identification of a location of the bolus in the two or more of the plurality of images;
    determination of a curve connecting the identified locations; and
    generating a representation of the curve in the composite image.

4. A system according to claim 3, wherein generation of the composite image comprises:
    identification of opposite edges of the bolus in the two or more of the plurality of images;
    determination of an outer contour of the vasculature based on the identified opposite edges; and
    generation of a representation of the outer contour in the composite image.

5. A system according to claim 1, wherein generation of the composite image comprises:
    identification of opposite edges of the bolus in the two or more of the plurality of images;
    determination of an outer contour of the vasculature based on the identified opposite edges; and
    generation of a representation of the outer contour in the composite image.

6. A system according to claim 1, wherein generation of the composite image comprises:

determination of foreshortening at a location of the vasculature based on a decreased size of the bolus and an increase in an intensity of the bolus at the location in an acquired image as compared to a size of the bolus and an intensity of the bolus in another of the acquired images.

7. A system according to claim 1, further comprising:
an X-ray detector and an X-ray source operable to acquire the plurality of images; and
a contrast injector to inject the bolus into the patient volume.

8. A system according to claim 1, the processing unit further to:
detect a second peak of an R-wave in a cardiac signal;
automatically inject a second bolus of contrast medium into a patient volume after expiration of a second predetermined injection delay period with respect to detection of the trigger event, wherein the second predetermined injection delay period is based on the period of the cardiac cycle, the predetermined injection delay period and an expected width of the bolus;
in response to detection of the second peak, automatically acquire a second plurality of images after expiration of the predetermined imaging delay period, two or more of the second plurality of images comprising an image of the bolus at respective different locations within vasculature of the patient volume; and
generate a composite image based on the first and second plurality of images, the composite image including a representation of the vasculature of the patient volume.

9. A system according to claim 8, wherein each of the plurality of images is acquired at a predefined imaging interval, and wherein a distance traveled by the bolus in the vasculature during the predefined imaging interval is greater than a dimension of the bolus in the direction of travel.

10. A system according to claim 1, further comprising:
an X-ray detector and an X-ray source operable to acquire the plurality of images;
a contrast injector to inject the bolus into the patient volume; and
a cardiac monitor to generate the cardiac signal.

11. A system according to claim 1, wherein the plurality of images are acquired from a first projection angle, and the processing unit further to:
in response to detection of the trigger event, automatically acquire a second plurality of images from a second projection angle after expiration of the predetermined imaging delay period, two or more of the second plurality of images comprising an image of the bolus at respective different locations within vasculature of the patient volume;
generate a second composite image based on the second plurality of images, the second composite image including a second representation of the vasculature of the patient volume;
generate a first two-dimensional skeleton based on the representation of the vasculature of the patient volume;
generate a second two-dimensional skeleton based on the second representation of the vasculature of the patient volume; and
generate a three-dimensional skeleton of the vasculature based on the first two-dimensional skeleton and the second two-dimensional skeleton.

12. A method comprising:
detecting a trigger event;
in response to detecting the trigger event, automatically injecting a bolus of contrast medium into a patient volume after expiration of a predetermined injection delay period;
in response to detecting the trigger event, automatically acquiring a plurality of images after expiration of a predetermined imaging delay period, two or more of the plurality of images comprising an image of the bolus at respective different locations within vasculature of the patient volume;
generating a composite image based on the plurality of images, the composite image including a representation of the vasculature of the patient volume; and
displaying the composite image,
wherein the detecting the trigger event comprises detecting a peak of an R-wave in a cardiac signal, wherein the imaging delay period is based on a time between the peak and the start of an S-T interval of the cardiac signal, and wherein the plurality of images are acquired during an S-T segment of the cardiac signal.

13. A method according to claim 12, wherein each of the plurality of images is acquired at a predefined imaging interval, and wherein a distance traveled by the bolus in the vasculature during the predefined imaging interval is greater than a dimension of the bolus in the direction of travel.

14. A method according to claim 12, wherein generating the composite image comprises
identifying a location of the bolus in the two or more of the plurality of images;
determining a curve connecting the identified locations; and
generating a representation of the curve in the composite image.

15. A method according to claim 14, wherein generating the composite image comprises:
identifying opposite edges of the bolus in the two or more of the plurality of images;
determining an outer contour of the vasculature based on the identified opposite edges; and
generating a representation of the outer contour in the composite image.

16. A method according to claim 12, wherein generating the composite image comprises:
determining foreshortening at a location of the vasculature based on a decreased size of the bolus and an increase in an intensity of the bolus at the location in an acquired image as compared to a size of the bolus and an intensity of the bolus in another of the acquired images.

17. A method according to claim 12, the further comprising:
detecting a second peak of an R-wave in a cardiac signal;
automatically injecting a second bolus of contrast medium into a patient volume after expiration of a second predetermined injection delay period with respect to detection of the trigger event, wherein the second predetermined injection delay period is based on the period of the cardiac cycle, the predetermined injection delay period and an expected width of the bolus;
in response to detecting the second peak, automatically acquiring a second plurality of images after expiration of the predetermined imaging delay period, two or more of the second plurality of images comprising an image of the bolus at respective different locations within vasculature of the patient volume; and generating a composite image based on the first and second plurality of images, the composite image including a representation of the vasculature of the patient volume.

18. A system comprising:
a cardiac monitor to generate a cardiac signal based on electrical signals received from a patient;
an x-ray detector and an x-ray source operable to acquire x-ray images;
a contrast injector to inject a bolus of contrast medium into the patient; and
a processing unit to:
  receive the cardiac signal from the cardiac monitor,
  detect a peak of an R-wave in a cardiac signal, wherein the plurality of images are acquired a trigger event;
  in response to detecting the peak, automatically injecting the bolus of contrast medium into the patient after expiration of a predetermined injection delay period;
  in response to detecting the peak, automatically acquiring a plurality of images during an S-T segment of the cardiac signal in response to expiration of a predetermined imaging delay period, the predetermined imaging delay period based on a time between the peak and a start of an S-T interval of the cardiac signal, where two or more of the plurality of images comprise an image of the bolus at respective different locations within vasculature of the patient; and
  generate a composite image based on the plurality of images, the composite image including a representation of the vasculature of the patient; and
a display to display the composite image.

19. A system comprising:
a processing unit to:
  detect a trigger event;
  in response to detection of the trigger event, automatically inject a bolus of contrast medium into a patient volume after expiration of a predetermined injection delay period;
  in response to detection of the trigger event, automatically acquire a plurality of images after expiration of a predetermined imaging delay period, two or more of the plurality of images comprising an image of the bolus at respective different locations within vasculature of the patient volume; and
  generate a composite image based on the plurality of images, the composite image including a representation of the vasculature of the patient volume; and
a display to display the composite image,
wherein the plurality of images are acquired from a first projection angle, and the processing unit further to:
  in response to detection of the trigger event, automatically acquire a second plurality of images from a second projection angle after expiration of the predetermined imaging delay period, two or more of the second plurality of images comprising an image of the bolus at respective different locations within vasculature of the patient volume;
  generate a second composite image based on the second plurality of images, the second composite image including a second representation of the vasculature of the patient volume;
  generate a first two-dimensional skeleton based on the representation of the vasculature of the patient volume;
  generate a second two-dimensional skeleton based on the second of the vasculature of the patient volume; and
  generate a three-dimensional skeleton of the vasculature based on the first two-dimensional skeleton and the second two-dimensional skeleton.

* * * * *